United States Patent
Mittelstadt

(10) Patent No.: US 6,337,211 B1
(45) Date of Patent: Jan. 8, 2002

(54) SYSTEM AND A METHOD FOR DETECTING ANTIFREEZING SUBSTANCES IN A HERMETIC COMPRESSOR

(75) Inventor: Friedrich Georg Mittelstadt, Joinville-SC (BR)

(73) Assignee: Empresa Brasileria de Compressores S./A-Embraco, Joinville-SC (BR)

( * ) Notice: Subject to any disclaimer, the term of this patent is extended or adjusted under 35 U.S.C. 154(b) by 0 days.

(21) Appl. No.: 09/381,168

(22) PCT Filed: Mar. 12, 1998

(86) PCT No.: PCT/BR98/00013

§ 371 Date: Sep. 29, 1999

§ 102(e) Date: Sep. 29, 1999

(87) PCT Pub. No.: WO98/40725

PCT Pub. Date: Sep. 17, 1998

(30) Foreign Application Priority Data

Mar. 12, 1997 (BR) ............................................. 9700384

(51) Int. Cl.⁷ .......................... G01N 21/77; F25B 49/02
(52) U.S. Cl. .......................... 436/167; 436/39; 436/100; 436/106; 436/113; 436/169; 436/181; 422/55; 422/56; 422/58; 422/86; 422/88; 62/125; 62/129
(58) Field of Search .......................... 436/39, 100, 164, 436/165, 167, 169, 181, 106, 113; 422/55, 56, 58, 83, 86, 88; 62/125, 127, 129

(56) References Cited

U.S. PATENT DOCUMENTS

| | | | |
|---|---|---|---|
| 4,014,216 A | * | 3/1977 | Thornton et al. ........ 73/863.23 |
| 4,022,578 A | | 5/1977 | Kretschmer |
| 4,096,734 A | | 6/1978 | Khayat |
| 4,110,998 A | * | 9/1978 | Owen .......................... 62/125 |
| 4,417,451 A | * | 11/1983 | Spauschus ................... 62/129 |
| 4,803,843 A | | 2/1989 | Otto |
| 4,923,806 A | | 5/1990 | Klodowski |
| 5,071,768 A | | 12/1991 | Klodowski |
| 5,174,124 A | * | 12/1992 | Paige et al. .................... 62/125 |
| 5,174,964 A | * | 12/1992 | Klodowski et al. ........... 422/88 |
| 5,345,774 A | | 9/1994 | Mount |
| 5,363,661 A | * | 11/1994 | Condit et al. .................. 62/77 |
| 5,377,496 A | | 1/1995 | Otto et al. |
| 5,550,061 A | | 8/1996 | Stone |
| 5,831,144 A | * | 11/1998 | Pastorello .................... 73/23.2 |
| 5,846,833 A | * | 12/1998 | Clough et al. ............... 436/139 |

FOREIGN PATENT DOCUMENTS

| | | |
|---|---|---|
| EP | 0 279 069 | 8/1988 |
| WO | WO 96/33394 | 10/1996 |

* cited by examiner

*Primary Examiner*—Maureen M. Wallenhorst
(74) *Attorney, Agent, or Firm*—Darby & Darby

(57) ABSTRACT

The invention relates to a system and a method for detecting antifreezing substances in a hermetic compressor.

12 Claims, 1 Drawing Sheet

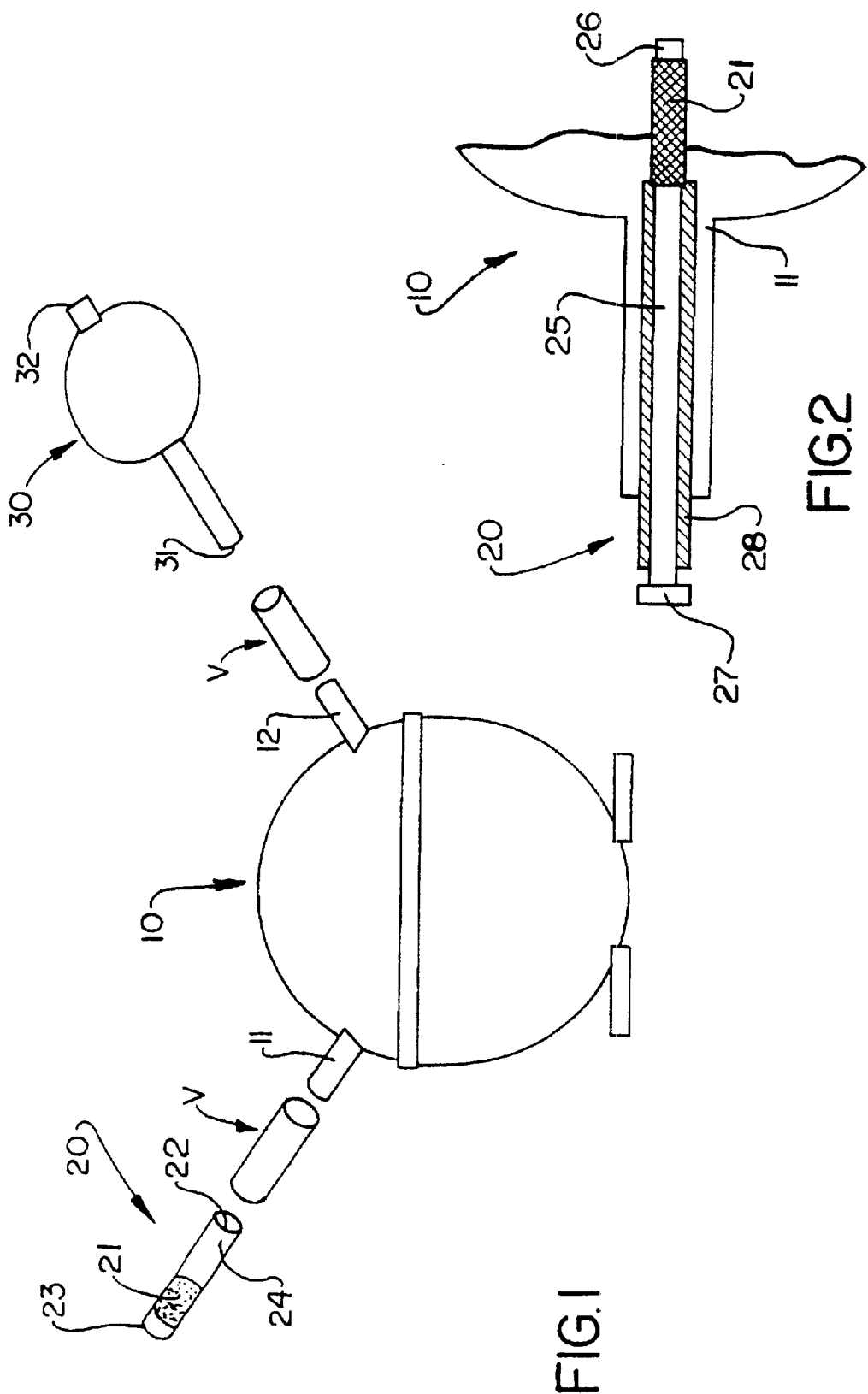

SYSTEM AND A METHOD FOR DETECTING ANTIFREEZING SUBSTANCES IN A HERMETIC COMPRESSOR

FIELD OF THE INVENTION

The present invention refers to a system and to a method for detecting the presence of antifreezing residues in a hermetic compressor, which has been removed from a refrigeration circuit.

BACKGROUND OF THE INVENTION

The presence of water in the circuit of a refrigeration system comprising a hermetic compressor may cause failure in the refrigeration system, due to clogs in the capillary tube of said system caused by the freezing of water inside this tube. The existence of water in the system results, for instance, when vacuum is not used for drying and eliminating the non-condensable substances from the refrigeration circuit before introducing the refrigerant fluid in said circuit.

In order to avoid failures in the system due to freezing, some technicians introduce in the refrigeration circuit an antifreezing fluid, among which the alcohols are the most common, although antifreezing substances in the form of ketones are also used. Among the ketones most used as an antifreezing substance is propanone (acetone). Other well known antifreezing substances are ammonia, inorganic salts, organic and inorganic acids, glicols, ethers, etc.

Though being able to allow the free flow of refrigerant fluid in the refrigeration circuit, the antifreezing substances are prejudicial to the refrigeration system, since they cause damages to the components of the compressor, leading to failure of the latter.

Several techniques are known for detecting antifreezing substances in compressors. Nevertheless, the application of these techniques require sophisticated and costly equipments, which are only available in large laboratories. Moreover, such techniques take a long time and further require that the compressor itself or a sample of its lubricant oil be transported to the laboratories provided with said equipments.

In function of the difficulty for detecting, in a practical, quick and safe manner, the presence of these antifreezing substances in the internal environment of the compressor, mainly due to the fact that said compressor has been opened and therefore a large part of its internal atmosphere carrying the antifreezing substance has dissipated to the environment, one cannot say that the operative failures of the compressor result from the undue utilization of the antifreezing substances.

This difficulty in detecting the presence of antifreezing substances in the compressor make the manufacturers substitute the compressors when an operative failure occurs during the guaranty period of said compressors.

DISCLOSURE OF THE INVENTION

Thus, it is an object of the present invention to provide a system and a method for detecting antifreezing substances in a compressor which has been removed from a refrigeration circuit, which allows to determine the presence of residues of antifreezing substances inside the compressor shell in a safe and unquestionable way.

A more specific object of the present invention is to provide a system and a method for the safe detection of antifreezing substances in a compressor, which is easy and practical to carry out and which may be achieved away from the operation site of the refrigeration system to which the compressor was connected, such as in a test installation.

The objectives mentioned above are achieved through a system for detecting antifreezing substances in a hermetic compressor, which has been removed from a refrigeration circuit and which comprises a hermetic shell having at least one nozzle, which communicates the inside of said shell with the environment and which comprises an antifreezing substance detecting means, containing at least one reactant, which is contactable with the atmosphere inside the shell through the nozzle, said antifreezing substance detecting means showing an alteration which is detectable when contacted by a determined amount of said antifreezing substance during a determined time interval, within which the determined amount of the antifreezing substance existing in the hermetic shell is able to cause the detectable alteration of the antifreezing substance detecting means.

The method for detecting the antifreezing substances in the system generally includes the following steps: connecting, to said nozzle, an antifreezing substance detecting means containing at least one reactant which will show a detectable alteration when contacted by a determined amount of said antifreezing substance; and contacting said antifreezing substance detecting means with the internal atmosphere of the compressor through the nozzle during a determined time interval, within which a determined amount of the antifreezing substance existing in the hermetic shell will cause the detectable alteration of the antifreezing substance detecting means.

BRIEF DESCRIPTION OF THE DRAWINGS

The invention will be described below, with reference to the appended drawings, in which:

FIG. 1 shows schematically a compressor, to which will be coupled an antifreezing substance detecting means according to a constructive form of the present invention; and FIG. 2 shows schematically another constructive form of the antifreezing substance detecting means of the present invention.

BEST MODE OF CARRYING OUT THE INVENTION

The present invention will be described in relation to the operation of a system for detecting an antifreezing substance in a compressor of a refrigeration circuit, said compressor having a hermetic shell 10 provided with at least one nozzle 11, which communicates the interior thereof with the environment and which is defined by one of the inlet and outlet tubes of the compressor.

According to the present invention, the system for detecting an antifreezing substance in a compressor removed from the refrigeration circuit comprises an antifreezing substance detecting means 20, containing at least one reactant for the antifreezing substance, to be contactable with the internal atmosphere of the hermetic shell 10 through the nozzle 11 thereof during a determined time interval, within which a determined amount of the antifreezing substance existing in the hermetic shell 10 is able to cause the detectable alteration of at least one reactant of the antifreezing substance detecting means 20.

According to the present invention, the antifreezing substance detecting means 20 includes at least one antifreezing substance detecting element, each said detecting element including at least one reactant support 21 containing a reactant mixture for one of the antifreezing substances defined, for example, by alcohols, ketones, ammonia, inorganic salts, organic and inorganic acids, glicols, ethers and others.

In the construction which employs a plurality of detecting means, the latter may be arranged relative to each other in series or parallely, for example, and mounted to the compressor shell, in order to be in contact with the inside of the hermetic shell of the compressor.

In a form of carrying out the invention, as illustrated in FIG. 1, the antifreezing substance detecting means 20 is provided with a detecting element having a gas inlet end 22 to be connected with the nozzle 11 of the hermetic shell 10 and an opposite end 23, which is, for example, opened.

In order to force the release of the gas containing the antifreezing substance to the gas mass provided inside the hermetic shell 10 and to allow the interaction of this gas with the antifreezing substance detecting means 20, the present system further comprises a gas impelling means 30, which is connected with the inside of the hermetic shell 10, so as to make the gas mass move therein. This movement may only occur with the compressor being agitated during the test, in order to release the particles of the antifreezing substance which are located inside the hermetic shell 10 and also aggregated to the lubricant oil of the compressor, as well as a preparation step of the compressor which precedes the actuation of the antifreezing substance detecting means 20.

In this construction, the gas impelling means 30 is provided with a connecting end 31, by which said gas impelling means 30 is operatively connected with the inside of the hermetic shell 10 through one of the parts defined by the hermetic shell 10 and the antifreezing substance detecting means 20, in order to provoke the displacement of the gas mass contained inside the shell towards the antifreezing substance detecting means 20.

According to the illustrations, the connecting end 31 of the gas impelling means 30 is mounted to another nozzle 12 of the hermetic shell 10, which nozzle is defined by one of the inlet or outlet tubes of the compressor 10, other than that which connects the antifreezing substance detecting means 20, said gas impelling means 30 being in the form of a pumping element, which is manually actuated, for example, and which has an opposite end 32, whereto is adjacently defined the pumping body thereof.

In a non-illustrated constructive option, the gas impelling means 30 causes the gas displacement towards the antifreezing substance detecting means 20, by drawing the gas contained inside the hermetic shell 10. In this case, the gas impelling means 30 is mounted to the hermetic shell 10 through the antifreezing substance detecting means 20.

According to the present constructive option, the antifreezing substance detecting means 20 and the gas impelling means 30 are mounted to the hermetic shell 10 through, e.g. a sealing means V, such as a silicone rubber tube.

In the construction which employs a plurality of detecting elements, the latter may be arranged relative to each other, so that the gas impelling means 30 forces the displacement of the gas mass contained inside the hermetic shell 10, sequentially or simultaneously, through one or more of said detecting elements.

According to the constructive form as illustrated in FIG. 1, the detecting element comprises a tubular body 24, inside which is disposed at least one reactant support 21 in the form of an absorbing element containing a reactant mixture to react with a determined antifreezing substance, for example a sponge, which is substantially saturated with said mixture in the liquid form.

According to another constructive form of carrying out the present invention, as illustrated in FIG. 2, the antifreezing substance detecting means 20 is in the form of a testing rod 25, which carries, at a testing end 26, at least one reactant support and which has an opposite end 27, used for grasping. In the illustrated constructive option, the testing rod 25 is located inside a supporting tube 28, which protects the reactant support 21 and through which the antifreezing substance detecting means 20 is mounted to the compressor.

In this construction, the antifreezing substance detecting means 20 is mounted to the nozzle 11 of the hermetic shell 10 of the compressor, so that the testing end 26 of the testing rod 25 be introduced and maintained inside the hermetic shell 10 during the time interval which is necessary for the reaction of the antifreezing substance with the antifreezing substance reactant of the reactant support 21. The movement of the air mass inside the hermetic shell 10, if necessary, occurs by manually agitating the testing rod 25 and consequently its testing end 26 inside said hermetic shell 10.

The presence of a determined amount of the antifreezing substance in the gas mass contained inside the shell causes a detectable alteration in the antifreezing substance detecting means 20, resulting, for example, in a visual alteration of permanent effect, such as color change, precipitation of crystals and separation of fluids.

In order that the minimum amount of the antifreezing substance be detectable by the antifreezing substance detecting means 20, in the constructive option containing the gas impelling means 30, the latter should provoke the displacement of the gas mass inside the hermetic shell 10 during a determined time interval, which is calculated to be sufficient so that said amount of antifreezing substance in the gas mass inside the hermetic shell 10 which is being displaced by the gas impelling means 30 interacts in the antifreezing substance detecting means 20, allowing the observation of a detectable alteration in said antifreezing substance detecting means 20.

Since the removal of the compressor from the refrigeration circuit results in loss of a substantial part of the gas inside the hermetic shell 10 to the environment, and together with this gas, the antifreezing substance inserted in the refrigeration circuit, for a better verification of the presence of residues of this antifreezing substance inside the hermetic shell 10, it is necessary that said antifreezing substance be agitated during a determined time interval (about 1 minute), for example before the impelling means is actuated, in order to mix a possible oil/antifreezing substance mixture, liberating the particles of said antifreezing substance to the internal atmosphere of the hermetic shell 10. The agitation may occur, for instance, before opening the inlet and outlet tubes of the compressor 10, thus preventing the lubricant oil, which is provided at the bottom of the inside of the shell, from reaching said inlet and outlet tubes.

According to the present invention, in order to detect the presence of antifreezing substances in the form of alcohols, the reactant mixture should include at least one positive ion, such as chrome 6+, cerium 4+ or manganese 7+, which is able to have a reduction reaction with the sample of the inner atmosphere of the compressor and produce a color change in the absorbing element provided in the testing element.

In the reaction with alcohol, chrome 6+ is reduced to chrome 3+; cerium 4+ to cerium 3+; and manganese 7+ to manganese 4+, each of said ions determining in this reaction a specific color to the absorbing element. Chrome 6+ may be obtained, for instance, from a solution of chromic acid and sulfuric acid or from a cichromate solution. Cerium 4+ may be obtained from a solution consisting of cerium hexanitrate and ammonium in an acid medium and the manganese 7+ may be obtained, for example, from a solution consisting of potassium permanganate in an acid medium.

In another possible reaction for detecting alcohols, the reactant mixture of the test element 20 contains a hydrochloric acid/zinc chloride solution. This reaction would result, if alcohol existed in the sample of the compressor atmosphere, in a separation of substances in the test element obtained with the occurrence of an immiscible phase composed by acyl chloride, generated from the volume of alcohol reacted with the mixture.

According to the present invention, for detecting the presence of antifreezing elements in the form of ketones, the reactant mixture should include at least one of the elements consisting of hydroxilamine hydrochloride, iodine, 2, 4-dinitrophenylhydrazine, phenylhydrazine and paraphenylhydrazine, but, in the case of the reaction of ketone, which is present in the gas mass inside the compressor, with hydroxilamine hydrochloride, hydrochloric acid is released, altering the color of the antifreezing element detecting means 20. The color change after the liberation of hydrocholoric acid occurs in the presence of a pH indicating element to be provided in the antifreezing element detecting means 20.

For detecting the presence of methylketones or compounds which are oxidizable therewith, the reactant mixture should include elemental iodine in a base medium which, in the reaction, forms iodite and iodoform with a substantial color change of the mixture.

The reactions of the ketones which are present in the gas mass inside the compressor shell with any one of the elements defined by 2, 4-dinitrophenylhydrazine, phenylhydrazine and paraphenylhydrazine will produce precipitates which are visually detectable in the antifreezing element detecting means 20.

What is claimed is:

1. A system for detecting antifreezing substances in a hermetic compressor, which has been removed from a refrigeration circuit, said compressor comprising a hermetic shell having at least one nozzle, which communicates the inside of said shell with the environment, said system comprising an antifreezing substance detecting means, containing at least one reactant, which is contactable with the atmosphere inside the shell through the nozzle, said antifreezing substance detecting means showing an alteration which is detectable when contacted by a determined amount of said antifreezing substance during a determined time interval, within which the determined amount of the antifreezing substance existing in the hermetic shell is able to cause the detectable alteration of the antifreezing substance detecting means, wherein the system further comprises a gas impelling means, which is operatively connected to the inside of said shell so as to cause the displacement of an air mass therewithin.

2. System, according to claim 1, wherein the antifreezing substance detecting means further comprises a gas inlet to be connected to the nozzle of the hermetic shell, in order to allow fluid communication with the inside of said shell, and wherein said gas impelling means causes the displacement of a gas mass contained inside the hermetic shell toward the antifreezing substance detecting means, during a determined time interval within which a determined amount of antifreezing substance existing in the hermetic shell is capable of causing a detectable alteration of the antifreezing substance detecting means.

3. System, according to claim 1, wherein the antifreezing substance detecting means further comprises at least one detecting element of a determined antifreezing substance and at least one reactant support containing a reactant mixture for reacting with an antifreezing substance selected from the group consisting of alcohols, ketones, ammonia, inorganic salts, organic acids, inorganic acids, glycols, and ethers.

4. System, according to claim 3, wherein the reactant support comprises an absorbing element.

5. System, according to claim 4, wherein the absorbing element is a sponge.

6. System, according to claim 5, wherein the antifreezing substance detecting means further comprises a testing rod having a testing end, which carries at least one reactant support and which is introduced inside the hermetic shell through the nozzle thereof.

7. System, according to claim 6, wherein the gas impelling means is connected to another nozzle of the hermetic shell wherein said another nozzle communicates the inside of said shell with the environment.

8. System, according to claim 3, wherein the reactant mixture comprises a positive ion, whose reduction reaction with the determined amount of antifreezing substance will produce a color change in the antifreezing substance detecting means.

9. System, according to claim 8, wherein the reactant mixture comprises one of the ions selected from the group consisting of chrome 6+, cerium 4+ and manganese 7+.

10. System, according to claim 3, wherein the reactant mixture comprises hydrochloric acid and zinc chloride.

11. System, according to claim 3, wherein the reactant mixture comprises one of the elements selected from the group consisting of hydroxilamine hydrochloride, iodine, 2,4-dinitrophenylhydrazine, phenylhydrazine and paraphenylhydrazine.

12. A method for detecting antifreezing substances in a hermetic compressor, which has been removed from a refrigeration circuit, said compressor comprising a hermetic shell having at least one nozzle communicating the inside of said shell with the environment, said method comprising:

a) connecting, to said at least one nozzle, an antifreezing substance detecting means containing at least one reactant which will show a detectable alteration when contacted by a determined amount of an antifreezing substance;

b) contacting said antifreezing substance detecting means with the internal atmosphere of the compressor through the at least one nozzle during a determined time interval, within which a determined amount of the antifreezing substance existing in the hermetic shell will cause the detectable alteration of the antifreezing substance detecting means;

c) connecting, to either the hermetic shell at another nozzle or the antifreezing substance detecting means, a gas impelling means; and d) agitating the compressor with the gas impelling means during a determined time interval, sufficient to release particles of the antifreezing substance, which are aggregated to the inner parts of the compressor, in order to cause the displacement of a gas mass containing the antifreezing substance towards the antifreezing substance detecting means during the determined time interval.

* * * * *